US011630101B2

(12) United States Patent
Nougier

(10) Patent No.: US 11,630,101 B2
(45) Date of Patent: Apr. 18, 2023

(54) METHOD FOR DIAGNOSING ANOMALIES IN THE COAGULATION OF BLOOD

(71) Applicant: Hospices Civils de Lyon, Lyons (FR)

(72) Inventor: Christophe Nougier, Saint Fons (FR)

(73) Assignee: HOSPICES CIVILS DE LYON, Lyons (FR)

( * ) Notice: Subject to any disclaimer, the term of this patent is extended or adjusted under 35 U.S.C. 154(b) by 787 days.

(21) Appl. No.: 15/776,203

(22) PCT Filed: Nov. 15, 2016

(86) PCT No.: PCT/EP2016/077722
§ 371 (c)(1),
(2) Date: May 15, 2018

(87) PCT Pub. No.: WO2017/085058
PCT Pub. Date: May 26, 2017

(65) Prior Publication Data
US 2020/0256847 A1    Aug. 13, 2020

(30) Foreign Application Priority Data
Nov. 16, 2015  (FR) ..................................... 1560945

(51) Int. Cl.
*G01N 33/49* (2006.01)
*G01N 27/07* (2006.01)

(52) U.S. Cl.
CPC ......... *G01N 33/4905* (2013.01); *G01N 27/07* (2013.01); *G01N 2800/224* (2013.01); *G01N 2800/52* (2013.01)

(58) Field of Classification Search
CPC ....... G01N 33/4905; G01N 33/86; C12Q 1/54
See application file for complete search history.

(56) References Cited

U.S. PATENT DOCUMENTS 3,699,437 A * 10/1972 Ur ........................... G01N 27/06
324/722
8,877,510 B2   11/2014 Calatzis et al.
(Continued)

FOREIGN PATENT DOCUMENTS

EP        2 182 345 A1    5/2010
WO     2013/143548 A1   10/2013

OTHER PUBLICATIONS

Multiplate whole blood impedance point of care aggregometry: Preliminary reference values in healthy infants, children, and adolescents S Halimeh, G de Angelis, A Sander, C Edelbusch, H Rott, S Thedieck, R Mesters, N Schlegel, U Nowak Gotti Klin Padiatr 2010; 222, 158-163 (Year: 2010).*

(Continued)

*Primary Examiner* — Lyle Alexander
*Assistant Examiner* — Dwan A Gerido
(74) *Attorney, Agent, or Firm* — Buchanan Ingersoll & Rooney PC

(57) ABSTRACT

The present invention relates to a method for diagnosing anomalies in the coagulation of blood, comprising the following successive steps: a) placing a sample of total blood in a holder containing two pairs of electrodes connected to an apparatus generating an electrical current; b) incubating this sample for 60 to 180 seconds in the presence of calcium; c) adding to this sample tissue factor in a concentration high enough to trigger the coagulation of the blood; d) measuring the impedance variation between the electrodes as a function of time, for a period comprised between 10 and 30 minutes from step (c), and generating a curve of the impedance values as a function of time; e) comparing the value of the area under the curve generated in step (d) with the value of an area under a reference curve.

20 Claims, 8 Drawing Sheets

(56) References Cited

U.S. PATENT DOCUMENTS

Figure 1:
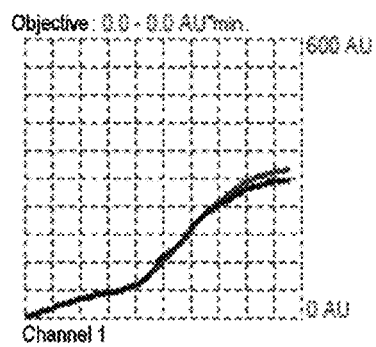
Figure 2:
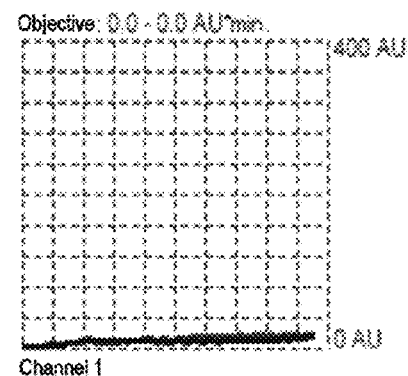
Figure 3:
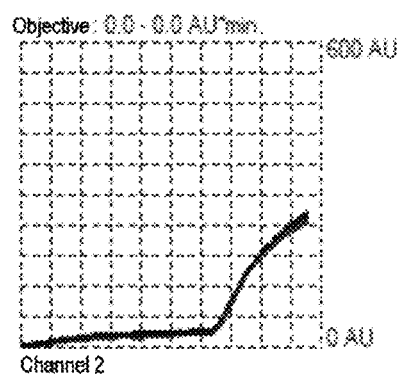

2008/0261261 A1* 10/2008 Grimes ............. G01N 33/4905
                                                        435/29
2009/0042217 A1*  2/2009 Brenner ............ G01N 33/4905
                                                        435/7.8

OTHER PUBLICATIONS

Whole blood coagulation thrombelastographic profiles employing minimal tissue factor activation B Sorensen, P Johansen, K Christiansen, M Woelke, J Ingerslev Journal of Thrombosis and Haemostasis, 1, 551-558 (Year: 2003).*

Multiplate Analyzer Operators Manual Mar. 2016 (Year: 2016).*

Faraoni et al., "Goal-directed Coagulation Management in the Perioperative Period of Cardiac Surgery," J. Cardiothorac. Vasc. Aneth., (Dec. 2013), vol. 27, No. 6. pp. 1347-1354.

Gerlach et al., "Hemostatic and hemorrhagic problems in neurosurgical patients," Acta Neuochir., (Jun. 26, 2009), vol. 151, No. 8, pp. 873-900.

Gölinger et al., "Coagulation management in patients undergoing mechanical circulatory support," Best Practice & Research Clinical Anaesthesiology, (Jun. 2012), vol. 25, No. 2, pp. 179-198.

Halimeh et al., "Multiplate whole blood impedance point of care aggregometry: Preliminary reference values in healthy infants, children and adolescents," Klin. Padiatr., (May 2010), vol. 222, No. 03, pp. 158-163.

Kind et al., "Is Dilutional Coagulopathy Induced by Different Colloids Reversible by Replacement of Fibrinogen and Factor XIII Concentrates?" J. Cardiothorac. Vasc. Anesth., (Nov. 2013), vol. 117, No. 5, pp. 1063-1071.

International Search Report dated Dec. 21, 2016, by the European Patent Office in corresponding International Patent Application No. PCT/EP2016/077722 with English translation.

* cited by examiner

Normal subject:

Subject with severe hemophilia:

Subject with mild hemophilia:

Subject with fibrinogen deficiency

Healthy subject:

Subject with hemophilia:

Healthy subject:

Subject with hemophilia:

Hemophilia

Hemophilia B

METHOD FOR DIAGNOSING ANOMALIES IN THE COAGULATION OF BLOOD

CROSS-REFERENCE TO RELATED APPLICATIONS

This application is a U.S. National Stage Application pursuant to 35 U.S.C. § 371 of International Patent Application PCT/EP2016/077722, filed on Nov. 15, 2016, and published as WO 2017/085085 on May 26, 2017, which claims priority to French Patent Application 1560945, filed on Nov. 16, 2015, all of which are incorporated herein by reference in their entireties for all purposes.

The present invention relates to a novel method for ex vivo evaluation of the process of blood clotting, specifically in order to diagnose coagulation anomalies such as hemophilic states or other clotting factor deficiencies based on a blood sample from a subject.

Blood clotting is a complex process that makes it possible to plug a gap in the endothelial wall of blood vessels in mammals.

Coagulation, or hemostasis, begins almost instantly after a lesion of the blood vessel wall. It is composed of three main steps:
1) Formation of a "platelet plug" by platelet aggregation in order to stop the bleeding: this is primary hemostasis.
2) Induction of a complex cascade of events during which plasma proteins referred to as "clotting factors" react to form fibrin fibers that reinforce the platelet plug: this is secondary hemostasis.
3) Destruction of the primary clot or fibrinolysis.

Numerous clotting disorders that lead to the risk of more extensive bleeding have been identified. Each of these clotting disorders is associated with a deficiency or anomaly in one of the factors involved in the cascade, manifesting clinically as hemorrhagic disorders that are classified as mild, moderate, or severe according to the severity of the deficiency or anomaly.

The disorders that cause clotting problems are referred to as the coagulopathies; among these, a distinction is made between those caused by a disorder of primary hemostasis and those caused by a defect in the clotting factors, either congenital or acquired.

The disorders of primary hemostasis include the thrombopenias, the thrombopathies, and von Willebrand disease.

Thrombopenia or thrombocytopenia is a significant decrease in the number of blood platelets below the threshold of 150,000 platelets per $m^3$.

The thrombopathies are associated with various platelet dysfunctions. They are most often acquired, caused by taking drugs (aspirin, nonsteroidal antiinflammatories, etc.). The congenital thrombopathies, which are hereditary, are much rarer.

Von Willebrand disease is the most common congenital disorder of primary hemostasis. It is caused by a quantitative or qualitative deficiency of von Willebrand factor (vWF), which allows platelets to adhere to the subendothelium.

The hemorrhagic diseases connected with clotting factors are either acquired, such as hepatocellular insufficiency, disseminated intravascular clotting, hypovitaminosis K, and the presence of anti-factor antibodies, such as in acquired hemophilia; or congenital, such as the hemophilias, deficiencies in clotting factors XI, VII, XIII, II, X, and hypofibrinogenemia or afibrinogenemia.

The hemophilias are associated with a congenital blood clotting anomaly related to a factor VIII deficiency (hemophilia A) or a factor IX deficiency (hemophilia B). The genetic anomaly responsible is located in the F8 or F9 gene. In a third of cases, hemophilia is caused by a de novo mutation; in the other cases, the mutation is transmitted by heredity.

Other rarer congenital anomalies involve factor XI, factor VII, factor XIII, factor X, or factor II deficiencies or a low level or absence of fibrinogen. The anomalies may be quantitative in cases resulting from a lack of or reduction in the concentration of the clotting factor or qualitative in cases where the clotting factor is present but poorly functional or non-functional.

The clinical symptoms of congenital clotting factor anomalies are chiefly bleeding symptoms, which may affect every organ. These symptoms are proportional to the severity of the clotting factor deficiency or defect. The disorder may be severe, with spontaneous hemorrhagic symptoms from the first year of life in a patient with severe hemophilia, or may show a more moderate clinical picture in the case of a moderate or mild deficiency.

The congenital fibrinogen deficiencies, which are rarer, are clotting disorders due to a reduction in the concentration and/or function of circulating fibrinogen and characterized by bleeding of varying severity.

Other hereditary deficiencies of clotting factor(s) have been described, but remain exceptional. In these cases as well, hemorrhagic symptoms are variable and depend on the severity of the anomaly.

PRIOR ART

Many tests for detecting blood clotting anomalies are currently known and routinely used by clinicians.

These tests are used for various purposes, in particular for diagnosing the disorders listed above, for following the effects of coagulant or anticoagulant treatment in a subject, or for screening potential coagulant or anticoagulant treatments.

Generally speaking, for hospital practitioners, a clotting anomaly in a subject must be detected before performing surgery on said subject in order to rule out the risk of bleeding.

In addition to platelet count, the Quick's prothrombin time (QT, also known as the prothrombin test PT) and activated partial thromboplastin time (APTT, also referred to as KAPTT if the activator used is kaolin) are the two tests most frequently used to detect a coagulopathy.

The QT allows the measurement of clotting time under in vitro conditions after activation by calcium thromboplastin (containing tissue factor in a high concentration—of the order of 4 to 6 nM—and pro-coagulant phospholipids). The result of the QT is 11 to 13 seconds for a sample of normal blood. Prolongation of this time indicates the presence of a clotting anomaly, in particular a congenital or acquired factor VII deficiency.

APTT (activated partial thromboplastin time) allows the measurement of clotting time under in vitro conditions, with the cephalin used containing an activator and pro-coagulant phospholipids. In adults, the reference value is 30 to 40 seconds. Significant prolongation of APTT indicates the presence of a clotting anomaly connected with hemophilia A or B, factor XI or XII deficiency, or the presence of anticoagulant therapy.

The thrombin time (TT) test allows the measurement of clotting time in blood plasma after the addition of thrombin and calcium. The reference value is about 20 seconds. This test measures the conversion of fibrinogen to fibrin; it is used in cases of hemorrhagic syndrome or in treatment using heparin or a thrombolytic agent. It is used less and less frequently today, except in the diagnosis of fibrinogen defects.

The thrombin generation test, a semi-automated method based on the use of a chromogenic or fluorogenic substrate, allows the measurement of thrombin generation in vitro after activation with tissue factor. This test, which is interesting because it is carried out under close to physiological conditions, is difficult to carry out because of the specific pre-test conditions required and a lack of standardization, and is thus limited to experienced laboratories.

The major drawbacks of these tests are their lack of sensitivity for moderate diseases on the one hand and their lack of specificity on the other; it is often necessary to carry out additional tests (determination of factors, assaying of circulating anticoagulant, etc.) in order to identify the origin of the clotting disorder observed.

Therefore, a "clotting profile" often includes several further tests in addition to QT and APTT, such as a fibrinogen assay, which is carried out by means of more specific tests in the case of an anomaly. This entails increased expenditure, both in terms of the reagents and material used and with respect to working time.

Moreover, a major drawback of the tests currently in use is that they must be carried out on platelet-poor plasma obtained from a whole blood sample after said sample has been centrifuged for 10 to 15 minutes. This limits the use of these tests in emergencies because of the additional time required for this centrifugation step and imposes an additional cost due to pre-treatment of the blood sample.

Among the tests that may be carried out on whole blood without centrifugation, one may mention activated clotting time (ACT); this test is not frequently used because it is suitable for only one indication, the monitoring of preoperative heparin therapy before cardiac surgery and neutralization thereof by protamine.

One may also mention whole blood thromboelastography (TEG), which allows complete investigation of the clotting process from the initial formation of the clot until its withdrawal and dissolution using special equipment. This method is based on monitoring of a pin that is permanently rotated, with blood clotting interfering with the movement of the pin. Rotational thromboelastometry (ROTEM®, Germany) allows several different tests to be carried out simultaneously by using specific reagents (Lang et al., 2005).

The drawback of this method is that it is necessary to use numerous reagents and carry out several tests in parallel in order to get an overall view of the various characteristics of clotting. Moreover, the sensitivity of this method for certain clotting anomalies, in particular hemophilia, is mediocre.

At present, there is no test that allows the identification of a subject suffering from a coagulopathy, and in particular a subject suffering from a hemophilic disorder, based on a single test.

Specifically, for hemophilia A or B, in addition to clinical symptoms, diagnosis is based on detection of the following:
- isolated prolongation of APTT in the absence of a circulating anticoagulant, combined with normal QT results;
- an isolated factor VIII or factor IX deficiency.

Moreover, there is no test that allows identification of a subject having a deficiency of another clotting factor based on a single test.

More generally, there is no comprehensive, rapid test that may be conducted with a small volume of whole blood without requiring an initial step of centrifugation and uses a single reagent that is capable of predicting hemorrhagic risk and detecting congenital or acquired clotting anomalies.

The availability of such a simple and rapid detection test would save time and be more economical from a medical standpoint in the investigation of anomalies of hemostasis.

FIGURES

FIGS. 1-4 and 6-7 show curves representing measurement of the impedance variation over time in whole blood samples, with this measurement being carried out using a Multiplate Analyzer®. The y axis represents the time, measured for a period of 20 minutes from addition of the tissue factor. The y axis represents the impedance variation in arbitrary units (AU).

FIG. 1. Sample from subject without a clotting anomaly.
Concentration of tissue factor: 2 pM
Area under the curve: 4703 AU/min FIG. 2. Sample from subject with severe hemophilia
Concentration of tissue factor: 2 pM
Area under the curve: 301 AU/min FIG. 3. Sample from subject with mild hemophilia
Concentration of tissue factor: 2 pM
Area under the curve: 2180 AU/min FIG. 4. Sample from subject with fibrinogen deficiency
Concentration of tissue factor: 2 pM
Area under the curve: 1173 AU/min FIG. 5. Summary diagram of distribution of values for area under the curve as a function of the populations studied. The values for area under the curve are indicated on the y axis in AUC (AU/min).

The populations represented are as follows: controls, subjects with severe hemophilia A (HA) and B (HB), subjects with moderate hemophilia A (HA) and B (HB), subjects with mild hemophilia A (HA) and B (HB), a subject with hypofibrinogenemia, and a subject presenting a mild factor XI deficiency.

FIG. 6. Test with tissue factor concentration of 100 pM
A) Sample from subject without clotting anomaly.
B) Sample from subject with hemophilia FIG. 7. Test with tissue factor concentration of 1 pM
A) Sample from subject without clotting anomaly.
B) Sample from subject with hemophilia FIG. 8. Correlation curve of level of plasma factor VIII activity (x axis) and area under the curve measured in the subjects (y axis)

The level of plasma factor VIII activity is less than 1% for the subjects with severe hemophilia A, 1 to 5% for the subjects with moderate hemophilia A, and 5 to 40% for the subjects with mild hemophilia A. The values above 40% were determined in samples from non-hemophilic subjects.

The correlation observed is excellent: $r^2=0.883$.

Figure 9:
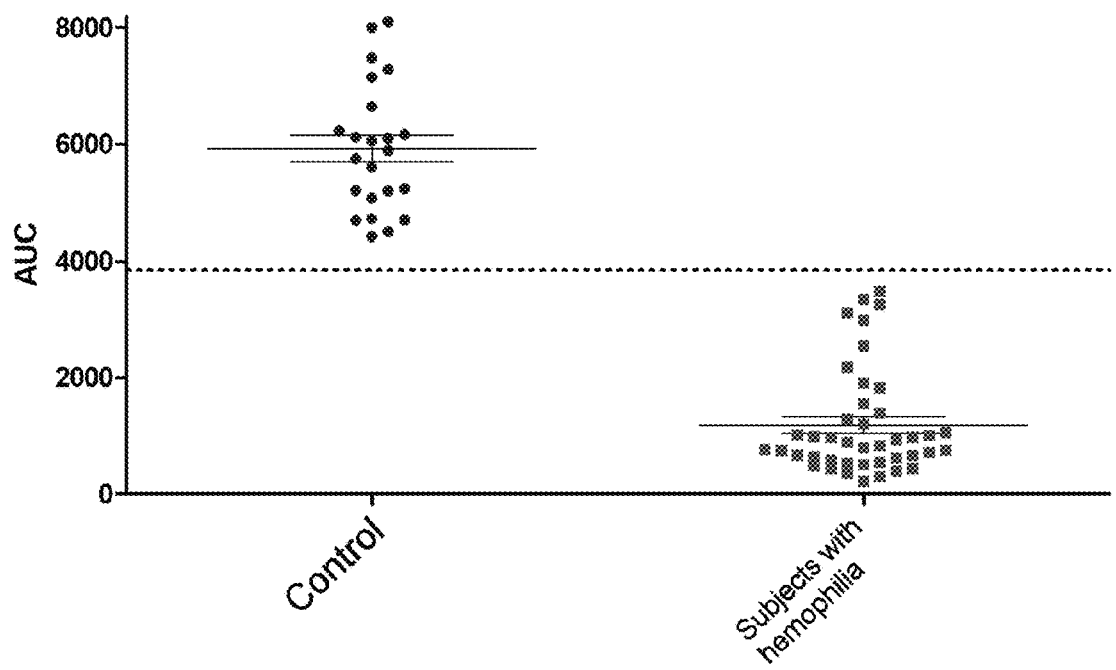

FIG. 9. Summary diagram of distribution of values for area under the curve according to the populations studied. The values for area under the curve are indicated on the y axis in AUC (AU/min).

The populations represented are as follows: controls and subjects with hemophilia, subjects with all types of hemophilia and mixed severity. The mean AUC of the controls is 5930; that of the hemophilic subjects is 1192. The statistical analysis result is highly significant ($p<0.0001$).

Figure 10:
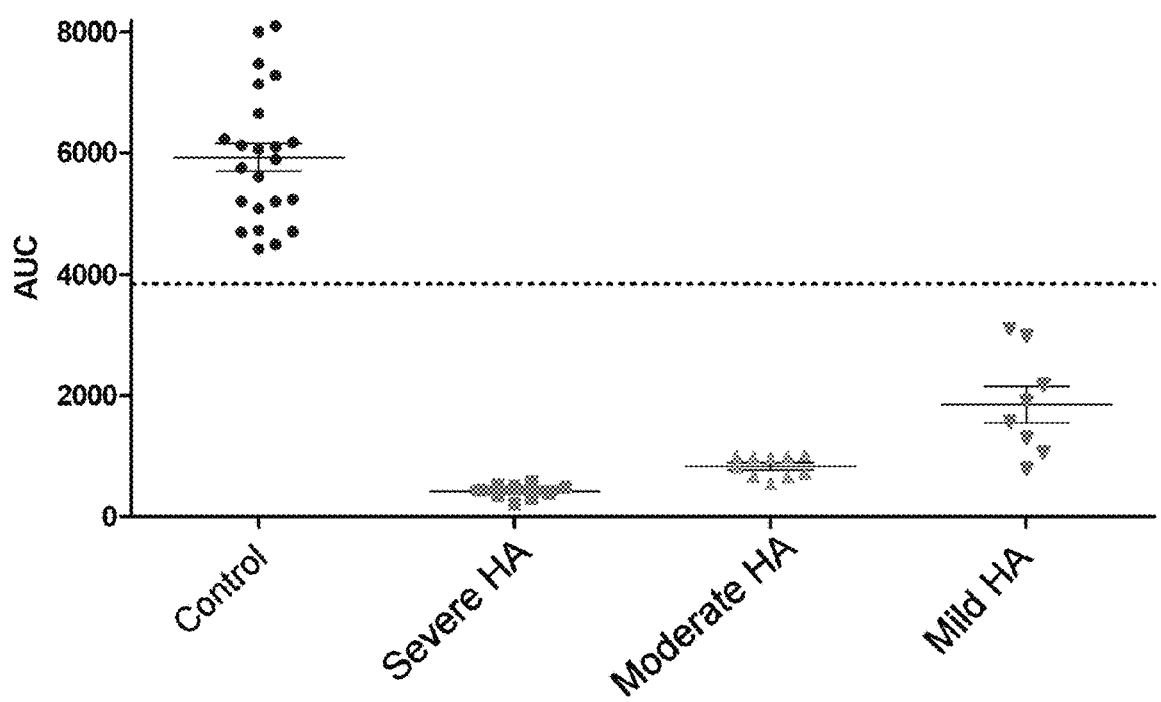

FIG. 10. Summary diagram of distribution of values for area under the curve according to the populations studied for the diagnosis of hemophilia A (HA). The values for area under the curve are indicated on the y axis in AUC (AU/min).

The populations represented are as follows: controls (number of subjects: 23); subjects with severe HA (number of subjects: 9); subjects with moderate HA (number of subjects: 10) and subjects with mild HA (number of subjects: 8).

Figure 11:
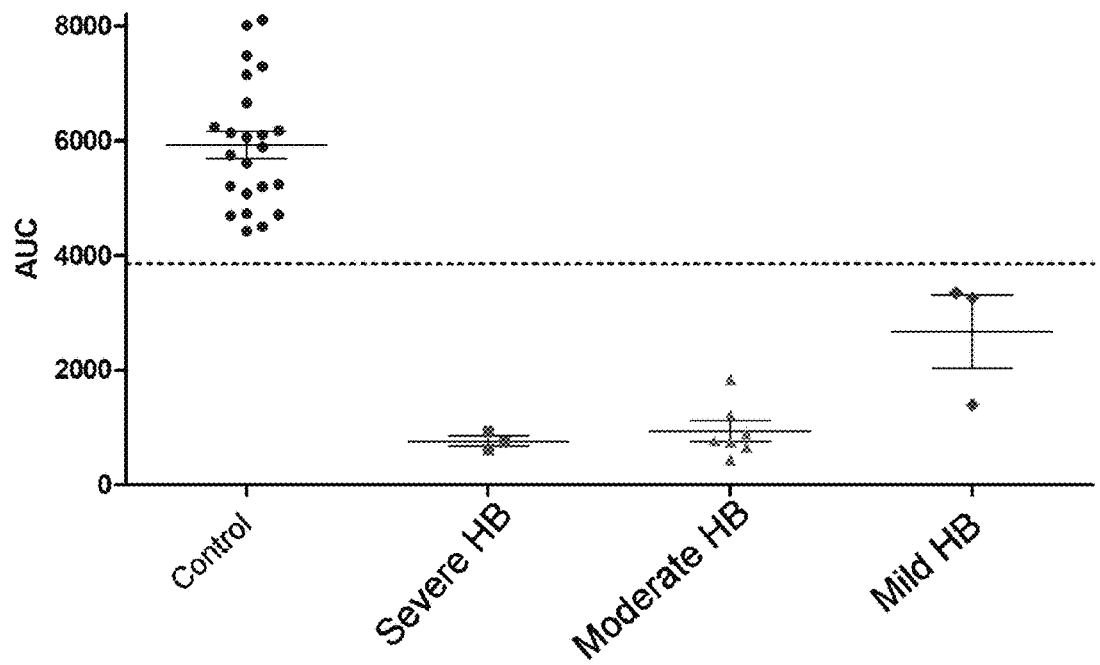

FIG. 11. Summary diagram of distribution of values for area under the curve according to the populations studied for the diagnosis of hemophilia B (HB). The values for area under the curve are indicated on the y axis in AUC (AU/min).

The populations represented are as follows: controls (number of subjects: 23); subjects with severe HB (number of subjects: 3); subjects with moderate HB (number of subjects: 7) and subjects with mild HB (number of subjects: 3).

Figure 12:
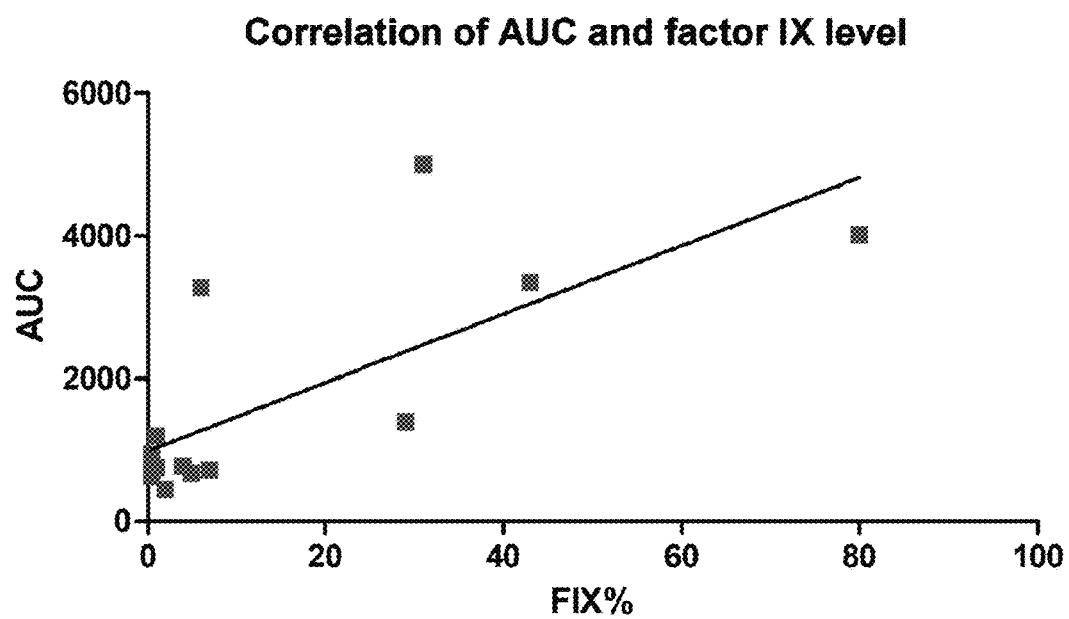

FIG. 12. Correlation curve of level of plasma factor IX activity (x axis) and area under the curve measured in the subjects (y axis) The level of factor IX activity is less than 1% for the subjects with severe hemophilia B, 1 to 5% for subjects with moderate hemophilia B, and 5 to 40% for the subjects with mild hemophilia B. The values above 40% were determined in samples from non-hemophilic subjects.

The correlation observed is favorable: r2=0.5417.

Figure 13:
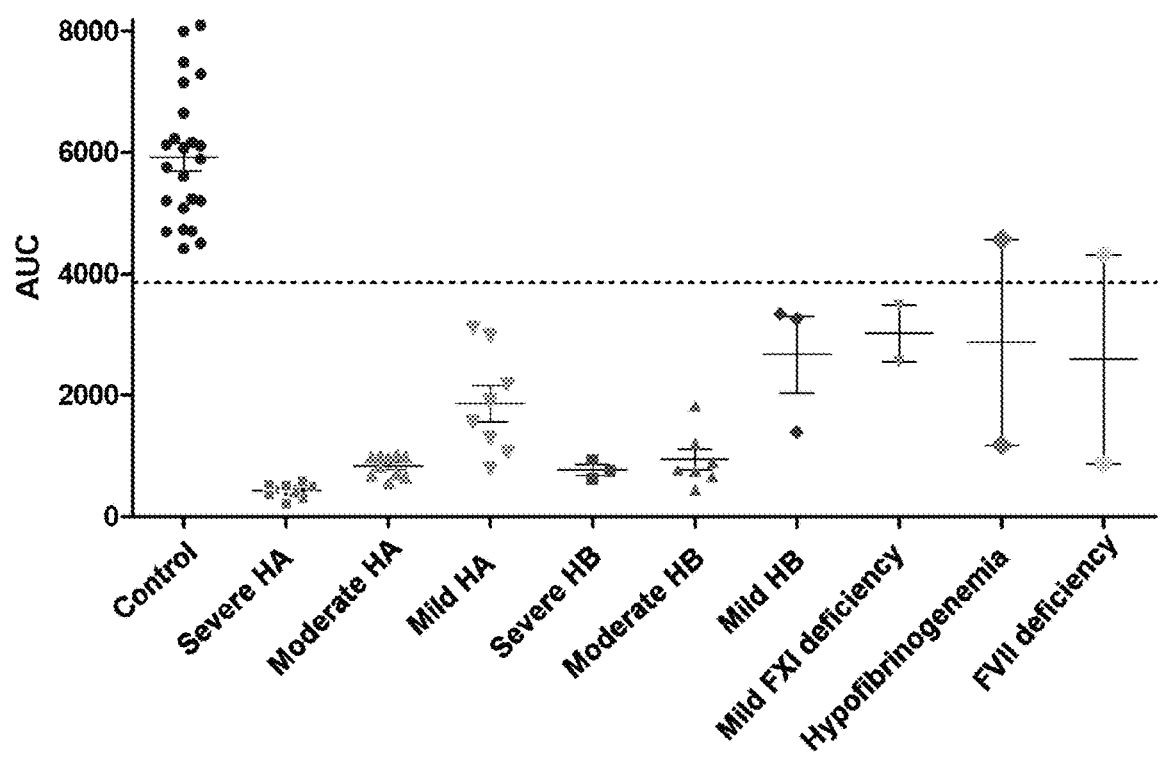

FIG. 13. Summary diagram of distribution of values for area under the curve according to the populations studied. The values for area under the curve are indicated on the y axis in AUC (AU/min). The numbers of subjects in each population are greater than in FIG. 5.

The populations represented are as follows: controls, subjects with severe hemophilia A (HA) and B (HB), subjects with moderate hemophilia A (HA) and B (HB), subjects with mild hemophilia A (HA) and B (FIB), subjects with a mild factor XI deficiency, subjects with hypofibrinogenemia, subjects with factor VII deficiency.

SUMMARY OF THE INVENTION

The present invention concerns a method for diagnosing anomalies in blood clotting based on measurement of impedance in a whole blood sample after adding a suitable concentration of tissue factor.

The present method is based on determination of a value for area under the curve, said curve representing the impedance variation measured over time between two electrodes immersed in a solution of whole blood, the clotting of which is initiated by adding a low concentration of tissue factor.

Determination of this value allows rapid, precise, and specific detection of whether a subject has a clotting anomaly and whether said anomaly is severe or moderate.

The present invention has the following advantages:
this diagnostic method is carried out using whole blood and is therefore rapid because it does not require centrifugation of the blood sample;
this method allows diagnosis by means of a single test of various blood clotting anomalies, in particular anomalies of secondary hemostasis;
this method does not require any additions to the existing equipment; in particular, it may be carried out on devices already used on a routine basis, such as the Multiplate Analyzer®;
this method is carried out using samples of low volume, in particular less than 1 ml, thus reducing the required sampling volume, which is particularly advantageous when the subjects are children.

Implementation of the present method makes it possible in particular to diagnose, by means of a single test, disorders of secondary hemostasis, in particular the hemophilias.

The present invention also relates to a method for monitoring individualized therapy of subjects suffering from a clotting anomaly, and in particular to a method for determining the efficacy of treatment of a blood clotting anomaly in a subject, comprising the following steps:
i) determining the value for the area under the curve of a blood sample from said subject before the beginning of said treatment, and
ii) determining the value for the area under the curve of a blood sample from said subject after the beginning of said treatment,
with said treatment being considered effective when the value for the area under the curve determined in step ii) is greater than the value for the area under the curve determined in step i).

DETAILED DESCRIPTION OF THE INVENTION

It is understood that the present method may be carried out on any type of apparatus or device comprising at a minimum a receptacle, two pairs of electrodes that may be immersed in the receptacle, and a device generating an electrical signal and capable of measuring the impedance variation between the electrodes.

This device preferably also allows the automatic generation of a curve of impedance values as a function of time.

According to a preferred aspect of the invention, the method according to the invention is carried out on a Multiplate Analyzer®.

Multiplate Analyzer®

There are devices which, because of the presence of two pairs of electrodes in the cuvette containing the blood sample, allow measurement of the impedance between the electrodes, said impedance being a function of the viscosity of the sample and therefore of the progress of the clotting process. One of these devices in particular is the Multiplate Analyzer®, also referred to as the Multiplate®, marketed by Roche.

The Multiplate® comprises single-use cuvettes in which a blood sample and a reagent are placed. The cuvette is inserted into the unit, and an electric current is then passed through the solution in contact with the electrodes. The impedance thus measured is related to the platelet aggregation of the blood sample and varies as a function thereof.

In particular, this apparatus is described in detail in the patent applications U.S. Pat. No. 8,877,510 and EP 2182 345.

The following tests have been conducted with the Multiplate® to date:

TABLE 1

| Code name of test | Complete description of test | Diagnostic purpose of test |
| --- | --- | --- |
| ADP + PGE1 = ADPtest HS | Aggregation induced by ADP and specific to the P2Y12 receptors, which are the target of the thienopyridines (inhibition of the other targets of ADP by PGE1) | Detection of resistance to APAs (antiplatelet agents) |
| ASPItest | Aggregation dependent on the cyclooxygenases, which may be inhibited by aspirin or other NSAIDs | |
| TRAPtest | Stimulation of aggregation via the thrombin receptors. Sensitive to the GpIIb/IIIa inhibitors | |
| COLLtest | Stimulation of aggregation by collagen | Detection of anomalies of primary hemostasis |
| ADPtest | Stimulation of aggregation by ADP | |
| RISTOhigh | Aggregation dependent on von | |

TABLE 1-continued

| Code name of test | Complete description of test | Diagnostic purpose of test |
|---|---|---|
| RISTOlow | Willebrand factor and the GpIb-IX platelet receptor Aggregation dependent on von Willebrand factor and the GpIb-IX platelet receptor: detection of hypercoagulability with low concentrations of ristocetin | |

As shown in Table 1, the known indications for the Multiplate Analyzer involve tests that allow measurement of platelet aggregation, i.e. evaluation of primary hemostasis. The apparatus is used in particular for tests of resistance to antiplatelet agents (APAs), for the detection of von Willebrand disease, and for the detection of the congenital thrombopathies (Glanzmann's thrombasthenia, Bernard-Soulier syndrome, secretory anomalies).

The present invention relates to novel use of this apparatus for carrying out an overall test for detecting hemostasis disorders, in particular for diagnosing disorders of secondary hemostasis and/or fibrinolysis.

The present invention thus relates to novel use of a device suitable for measuring the impedance variation in a whole blood sample in order to diagnose disorders of secondary hemostasis and/or fibrinolysis.

More particularly, the present invention concerns a method for diagnosing anomalies in blood clotting, comprising the following successive steps:
  a) placing a whole blood sample in a receptacle containing two pairs of electrodes connected to a device generating an electric current;
  b) incubating this sample for 60 to 180 seconds in the presence of calcium;
  c) adding to this sample tissue factor in a concentration sufficient to initiate blood clotting;
  d) measuring the impedance variation between the electrodes as a function of time for a period of 10 to 30 minutes from step (c) and generating a curve of the impedance values as a function of time;
  e) comparing the value for the area under the curve generated in step (d) with a value for the area under a reference curve.

Optimum Conditions for Implementation

The present invention is based on the use of a device generating an electric current that allows measurement of the impedance variation between electrodes immersed in a whole blood sample ex vivo.

Electrical impedance is the measure of the opposition that an electrical circuit presents to an alternating sinusoidal current. The impedance variation is therefore also referred to as the Coulter Principle, from the name of its inventor. It corresponds to the electrical resistance of the blood sample, which varies during the clotting process.

Within the meaning of the present invention, the terms 'cup,' 'cuvette,' and 'receptacle' are used interchangeably to refer to the container in which the whole blood sample is placed and in which measurement of the impedance variation is carried out.

It is understood that in implementing the method according to the invention, the blood sample tested is maintained at a temperature of about 37° C. so that clotting may take place under conditions as close as possible to physiological conditions.

The presence of an agitator in the receptacle is optional, but this is preferable for implementing the invention.

Moreover, as is well known to the person skilled in the art, the presence of calcium in the blood sample is necessary for carrying out the method.

Calcium plays an indispensable role in the clotting cascade, and in particular in formation of the platelet plug. Specifically, in the platelets, calcium activates protein kinase C, which in turns activates phospholipase A2, which modifies the integrin glycoprotein IIb/IIIa, increasing its affinity for fibrinogen. The platelets thus activated are modified in shape: they change from spherical to star-shaped, and the fibrin interspersed in the glycoprotein IIb/IIIa allows aggregation of the platelets. Calcium also allows binding of clotting factors to the phospholipids expressed at the surface of platelets activated during the clotting process.

According to a preferred aspect of the invention, a saline solution comprising calcium is added to the sample in step (b), preferably by carrying out a vol/vol dilution.

This solution is selected among the calcium-containing saline solutions well known to the person skilled in the art, such as a solution of $NaCl/CaCl_2$ or a solution of PBS supplemented with calcium.

In step (b) of the process, the sample is incubated for 60 to 180 seconds, preferably 90 to 150 seconds, and more preferably for 120 seconds. This "pre-incubation" allows homogenous mixing of all of the clotting factors and stabilization of the temperature (37° C.) of the blood sample placed in the cup.

Tissue Factor

The above measures carried out with the Multiplate® Analyzer were performed after initiating the aggregation process using compounds selected in particular among arachidonic acid (ASPI), thrombin receptor-activating peptide (TRAP), collagen, and adenosine diphosphate (ADP).

In carrying out the method according to the invention, the clotting reaction is initiated by adding a low concentration of tissue factor.

The tissue factor added to whole blood in the presence of calcium initiates generation of the first traces of thrombin. The thrombin generated activates the platelets contained in the blood; these then aggregate at the electrodes, resulting in modification of the electrical signal between the electrodes. The clotting that follows platelet aggregation makes it possible to generate a fibrin network that also modifies the signal between the two electrodes. The measurement of impedance as a function of time is represented by a reaction curve.

The method according to the invention comprises the addition, in step (c), of tissue factor in a concentration sufficient to initiate blood clotting.

Within the meaning of the present invention, the expression "a concentration sufficient to initiate blood clotting" refers to a final concentration of tissue factor added to the receptacle, thus allowing initiation of the clotting process.

Example 3 below shows the results obtained by adding two different concentrations: 100 pM and 1 pM of tissue factor (FIGS. 6A, 6B, and 7A, 7B respectively). These two concentrations are sufficient for initiating blood clotting in the blood sample tested.

Figure 7A:
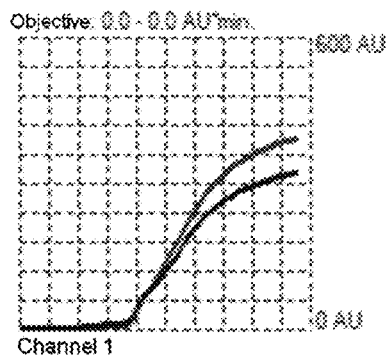
Figure 7B:
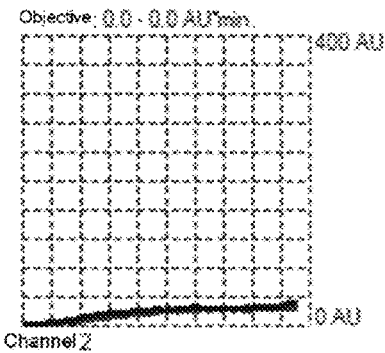

It has been observed that the signal obtained, i.e. the value for the area under the curve, is proportional to the concentration used. It has thus been observed that when the tissue factor is added in a final concentration of 1 pM, the results obtained with a sample from a healthy subject and a sample from a subject with hemophilia are more clearly distinguishable than with higher concentrations (FIGS. 7A and 7B).

According to a preferred embodiment of the invention, the tissue factor is added to the sample in a final concentration of 0.5 and 5 pM, it being understood that the bounds of the indicated interval are included in the range of preferred concentrations.

In particular, the tissue factor may be used in a concentration of 0.5 pM, 0.8 pM, 1 pM, 1.5 pM, 2 pM, 2.5 pM, 3 pM, 3.5 pM, 4 pM, 4.5 pM, or 5 pM.

According to a preferred aspect, the tissue factor is added to the sample in a final concentration of 1 pM or 2 pM.

In other clotting tests such as the QT test, the tissue factor is used in concentrations of about 4 nM, i.e. a concentration much greater than that used in the method according to the present invention.

In implementing the present invention, the tissue factor is added in a concentration lower than that used in other tests, but nevertheless sufficient to initiate blood clotting.

Measuring Time

The method is carried out by measuring the impedance variation of the blood sample in the presence of tissue factor, from the time of addition of this tissue factor, for a period of 10 to 30 minutes, and preferably 15 to 25 minutes. This measurement period, which is longer than that previously used with the Multiplate® device, makes it possible to obtain higher values for area under the curve, which therefore allows a clearer distinction between the values observed for the samples obtained from subjects with a coagulation anomaly and those observed for the samples obtained from healthy subjects.

According to a preferred embodiment of the invention, measurement of the impedance variation is carried out for a period of about 20 minutes.

In particular, the inventors found that from 30 minutes on, the results could no longer be used, because the blood samples coagulated even in the absence of tissue factor.

Blood Samples

The human blood samples are obtained according to the usual methods by qualified investigators. In particular, such samples are taken in medical test laboratories, hospitals, or clinics, or on an outpatient basis, in particular in mobile health units.

The term "whole blood" refers to blood that has not been centrifuged and therefore contains all of the cells, in particular the red cells, present in the blood.

The samples taken are placed in tubes containing reversible anticoagulants, which allow dilution of the blood to be maintained outside of the body, such as citrate or CTI (corn trypsin inhibitor).

According to a particular aspect of the invention, the blood sample is said to be "citrated," which means that it contains citrate as a reversible anticoagulant.

According to a preferred embodiment of the method according to the invention, the whole blood sample is citrated.

According to another embodiment of the invention, the volume of the whole blood sample is less than 1 ml, and preferably less than 500 µl. In particular, the sample tested may have a volume of about 300 µl.

Reference Curve

It is understood that determination of a reference curve indicating the normal expected response of a blood sample to the addition of tissue factor, reflecting a normal clotting process, is essential for carrying out the method according to the invention.

This reference curve can easily be determined by the person skilled in the art based on his or her general knowledge. Specifically, such a curve is prepared based on blood samples from subjects not having blood clotting disorders, or on the contrary from subjects having a specific and known blood clotting disorder.

According to a particular embodiment of the invention, the reference curve is a mean curve obtained by carrying out steps (a) through (d) of the method on blood samples from subjects without a clotting anomaly and calculating the arithmetic mean of each of the values obtained in step (d).

According to another embodiment of the invention, the reference curve is the curve obtained by carrying out steps (a) through (d) of the method on a blood sample from a single subject without a clotting anomaly.

In particular, each measurement may be carried out in duplicate in the same reaction receptacle, and the arithmetic mean of each measurement is the value used to prepare the reference curve.

According to another embodiment of the invention, the reference curve is the curve obtained by carrying out steps (a) through (d) of the method on a blood sample from a single subject suffering from a specified clotting anomaly, such as a "mild," "moderate," or "severe" anomaly.

According to another embodiment of the invention, the reference curve is the curve obtained by carrying out steps (a) through (d) of the method on blood samples from subjects with a specified clotting anomaly, such as a "mild," "moderate," or "severe" anomaly, and calculating the arithmetic mean of each of the values obtained in step (d).

Based on these reference curves, the value for the area under the reference curve may easily be determined by calculating the surface delimited by the curve and based on the x axis. The numerical value of this "area under the curve" is compared with the area measured under the reference curve, also referred to as the "reference value."

A mean reference value may be specified, with said "threshold" value clearly separating the values obtained from the blood samples of the controls, without any clotting anomaly, from those of the subjects with a coagulopathy.

This "threshold" reference value, also referred to as a "cut-off value," is determined based on (i) the values for area under the curve determined in subjects without a coagulopathy and (ii) the values for area under the curve determined in subjects with a coagulopathy.

As this value for area under the curve is based on arbitrary units, it can be defined in a numerical manner without difficulty by the person skilled in the art during implementation of the invention.

Step (e) of the method consists of comparing the value for the area under the curve generated in the previous step with the value for the area under the reference curve.

According to a particular embodiment of the invention, the impedance variation is measured once per minute to generate the curve.

Advantageously, the impedance variation is measured once every second, once every 2 seconds, once every 5 seconds, once every 10 seconds, once every 15 seconds, once every 20 seconds, once every 30 seconds, or once per minute.

As the variation of impedance is measured using arbitrary values, each investigator determines a reference curve and a reference value depending on the type of equipment used for carrying out the method according to the invention.

Generally speaking, the following relationship may be defined: if the value for the area under the curve of a sample is less than or equal to the value for the area under the reference curve, with the variation calculated being at least two standard deviations, it may be concluded that the subject from whom the present sample was taken probably has a coagulopathy.

As each subject is unique, it is understood that the values observed for area under the curve may vary slightly from the reference value, by an amount less than or equal to a standard deviation, without this being caused by a clotting anomaly.

Within the meaning of the invention, a standard deviation is defined as the square root of the variance, the latter being calculated according to the following mathematical formula:

$$\text{Variance} = \text{mean}(vi^2) - me.^2,$$

where vi denotes each value of area under the curve for each sample and me. denotes the arithmetic mean of the values for area under the curve.

Figure 5:
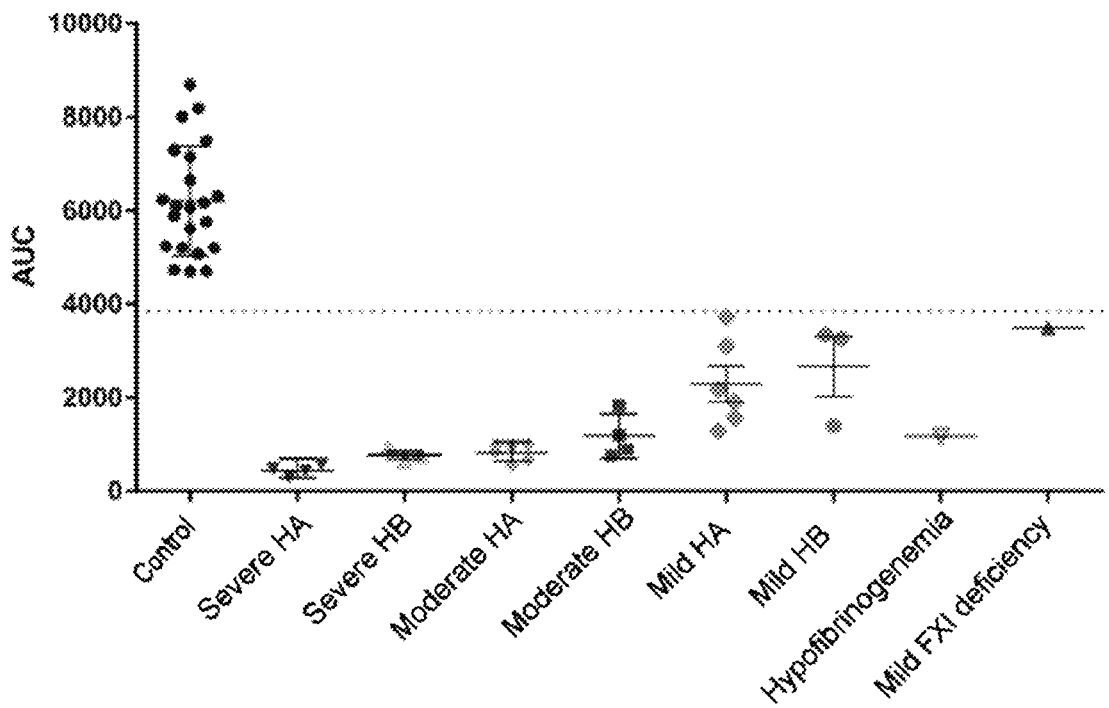

The values for area under the curve obtained from samples taken from various subject populations are shown in FIGS. 5 and 13. In these figures, each individual AUC value is represented by a dot; the mean of the values obtained in each group of subjects is indicated by a horizontal line; and two other shorter lines, one above and one below the mean, represent the standard deviation observed around this mean value.

It may be clearly seen that the blood samples from the subjects having severe deficiencies show values for area under the curve that are sharply lower than those observed for the blood samples from the subjects with mild deficiencies and far lower than those seen for the blood samples from the control population not suffering from clotting anomalies.

Disorders of Hemostasis and Monitoring of Coagulant Treatment

The method according to the invention makes it possible to diagnose blood clotting anomalies.

Advantageously, the method according to the invention also makes it possible to determine the severity of the blood clotting anomaly and to distinguish severe and mild cases.

The classification of the hemophilias according to their severity is shown in Table 2 below:

TABLE 2

| | Classification | Coagulant activity | Hemorrhagic symptoms |
|---|---|---|---|
| HEMOPHILIA | Severe | <1% of normal activity | Frequent bleeding, sometimes spontaneous, chiefly at articular and muscular sites |
| | Moderate | 1-5% of normal activity | Occasional bleeding, in particular in connection with trauma or surgery |
| | Mild | >5-40% of normal activity | Bleeding during severe trauma or surgery |

Therefore, the invention also relates to a method for determining the severity of a clotting anomaly in a subject, comprising the following steps:
  a) placing a whole blood sample in a receptacle containing two pairs of electrodes connected to a device generating an electric current;
  b) incubating this sample for 60 to 180 seconds in the presence of calcium;
  c) adding to this sample tissue factor in a concentration sufficient to initiate blood clotting;
  d) measuring the impedance variation between the electrodes as a function of time for a period of 10 to 30 minutes from step (c) and generating a curve of the impedance values as a function of time;
  e) comparing the value for the area under the curve generated in step (d) with reference values determined in subjects with mild, moderate, or severe coagulopathy.

The reference values are the values for area under the curve determined in subjects with a severe, mild or moderate clotting anomaly.

It is thus possible to determine the severity of the clotting anomaly observed in the subject tested.

Advantageously, the diagnosed clotting anomalies are disorders of secondary hemostasis, for which there was no single test available to date. The diagnosis could only be made after multiple tests and assays before concluding that such an anomaly was present.

The term "disorders of secondary hemostasis" refers to disorders connected with clotting factor deficiencies or defects; these disorders may be congenital or acquired.

Therefore, the disorders of secondary hemostasis that may be diagnosed using the method according to the invention are in particular selected among:
  the congenital coagulopathies: hemophilia A or B, deficiencies of other clotting factors such as factor XI, VII, XIII, X, V, II and fibrinogen, and
  the acquired coagulopathies, caused by taking coagulation inhibitors, in particular in the framework of anticoagulant therapy.

According to a particular aspect of the invention, the clotting disorders diagnosed are disorders of fibrinolysis, which constitutes the final stage of the clotting cascade.

According to a particular aspect of the invention, the clotting anomalies that may be diagnosed by the method according to the invention are disorders of secondary hemostasis and/or fibrinolysis.

The method according to the invention further allows monitoring of therapeutic treatments, in particular coagulant or anticoagulant treatments, administered to subjects with a clotting anomaly. Such treatments are referred to in the following as "treatment of a blood clotting anomaly."

Such coagulant treatments are administered, often for long periods, to subjects with a clotting anomaly.

In particular, the present invention relates to a method for determining the efficacy of treatment of a blood clotting anomaly in a subject, comprising the following steps:
  i) determining the value for the area under the curve of a blood sample from said subject before the beginning of said treatment by carrying out steps (a), (b), (c), and (d) of the method described above, and
  ii) determining the value for the area under the curve of a blood sample from said subject after the beginning of said treatment by carrying out steps (a), (b), (c), and (d) of the method described above,
with said treatment being considered effective when the value for the area under the curve determined in step ii) is greater than the value for the area under the curve determined in step i).

According to a particular aspect of the invention, said method for determining the efficacy of treatment or a hemophilic state in a subject comprises the following steps:
  i) determining the value for the area under the curve of a blood sample from said subject at a time $T_1$ after the beginning of said treatment by carrying out steps (a), (b), (c), and (d) of the method described above, and
  ii) determining the value for the area under the curve of a blood sample from said subject at a time $T_2$, after the first time $T_1$, by carrying out steps (a), (b), (c), and (d) of the method described above,
with said treatment being considered effective when the value for the area under the curve determined in step ii) is greater than the value for the area under the curve determined in step i).

Finally, the present invention also concerns a method for screening therapeutic molecules capable of acting on the clotting process, comprising the following steps:
i) obtaining two blood samples from the same subject treated with a candidate therapeutic molecule, one before the treatment and one during or after the treatment;
ii) determining the value for the area under the curve of the blood sample obtained before the beginning of said treatment by carrying out steps (a), (b), (c), and (d) of the method described above,
iii) determining the value for the area under the curve of the blood sample obtained during or after said treatment by carrying out steps (a), (b), (c), and (d) of the method described above, and
iv) comparing the values obtained in steps (ii) and (iii) in order to determine the effect of the treatment with said therapeutic molecule.

EXAMPLES

Example 1. Experimental Protocol

300 µl of a solution of NaCl/CaCl$_2$ (Roche Diagnostic) are placed in the cup before adding 300 µl taken from a citrated tube with a concentration of 0.107 M or 0.109 M. The cup is equipped with a magnetic bar for agitation and two pairs of silver electrodes connected to the Multiplate® unit (Roche Diagnostic).

After incubation for 120 seconds, clotting is initiated by adding a solution of tissue factor diluted in HEPES buffer; the final concentration in the sample is 2 pM (FIGS. 1 through 4), 100 pM (FIGS. 6A, 6B), or 1 pM (FIGS. 7A, 7B).

Measurement of the impedance variation between the electrodes (expressed in arbitrary units—AU) is carried out for a period of 20 minutes. A curve is thus generated as a function of time, and the curve thus obtained defines an area under the curve measured in AU/min (indicated in the figures as 'AUC').

Example 2. Results Obtained by Adding Tissue Factor in a Concentration of 2 pM

Figure 4:
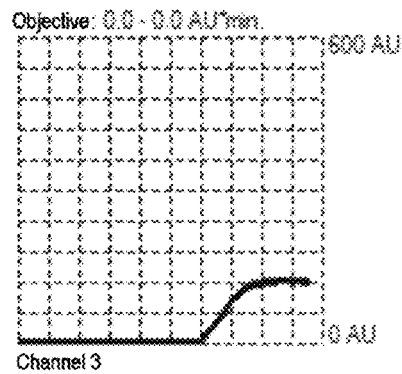

FIGS. 1 through 4 respectively show the following:
the curve obtained for a blood sample from a subject with no clotting disorders; the area under the curve is 4703 AU/min (FIG. 1.)
the curve obtained for a blood sample from a subject diagnosed with severe hemophilia; the area under the curve is 301 AU/min. (FIG. 2.)
the curve obtained for a blood sample from a subject diagnosed with mild hemophilia; the area under the curve is 2180 AU/min. (FIG. 3.)
the curve obtained for a blood sample from a subject diagnosed with a fibrinogen deficiency; the area under the curve is 1173 AU/min. (FIG. 4.)

It may therefore be deduced from these curves that when the area under the curve is less than a threshold value referred to as a "reference value," a clotting anomaly is present.

FIG. 5 shows the distribution of values for area under the curve as a function of the characteristics of the subjects tested.

In the present case, a threshold value of 4000 arbitrary units/min (AUC) was determined, which distinguishes:
the values around 6000 AUC, characteristic of the controls, who do not have a clotting anomaly, from
the values less than or equal to 4000 AUC, characteristic of the subjects with a clotting anomaly, even mild; among these subjects, those suffering from a severe anomaly show values for area under the curve of less than 2000 AUC.

FIG. 13 was prepared according to the same experimental protocol as FIG. 5, with the only modifications being the addition of 1 pM of tissue factor to the reaction medium and the larger number of blood samples tested.

In this experiment, it was possible to test two blood samples from subjects with a factor VII deficiency. The results are consistent with those shown in FIG. 5.

In these figures, each individual AUC value is represented by a dot; the mean of the values obtained in each group of subjects is indicated by a horizontal line; and two other shorter lines, one above and one below the mean, represent the standard deviation observed around this mean value.

Example 3. Adjustment of Concentration of Tissue Factor Required for Initiating Clotting Experiments were conducted according to the same protocol as that described in example 1 in order to determine the optimum concentration range of tissue factor sufficient to initiate blood clotting in vitro in the test described in the present application.

Two concentrations were tested: 100 pM and 1 pM, in two types of blood samples: one from a healthy subject without a clotting anomaly (A) and the other from a subject with moderate hemophilia.

Figure 6A:
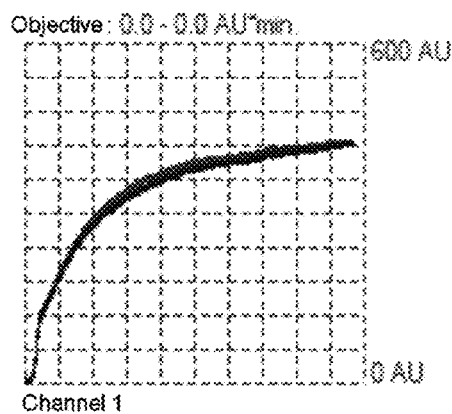
Figure 6B:
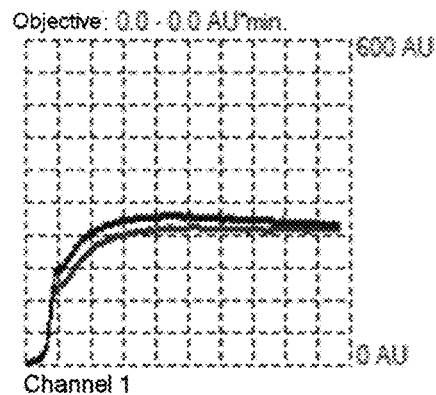

When clotting is initiated with a concentration of 100 pM of tissue factor, the values for area under the curve are elevated and distinguishable between the two subjects:
17,191 AU/min for a healthy subject with no clotting disorder;
11,638 AU/min for a subject with hemophilia. (FIG. 6A, 6B)

When clotting is initiated with a concentration of 1 pM of tissue factor, the values for area under the curve are less elevated and are more sharply distinguishable between the two subjects:
4,838 AU/min for the healthy subject not having a clotting disorder;
524 AU/min for the subject with hemophilia. (FIG. 7A, 7B)

With this concentration of tissue factor, the difference in values between the two subjects is quite clear, with the subject with hemophilia showing a value for area under the curve that is less than 15% of the value for area under the curve of the healthy subject; here, this curve constitutes the reference curve.

Figure 8:
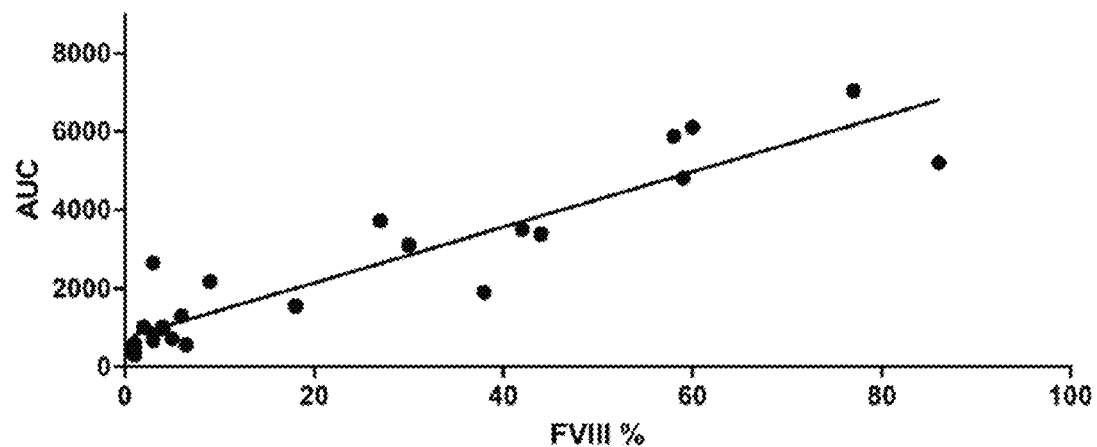

Example 4. There is a Direct Correlation Between the Factor VII Level and the Value for Area Under the Curve FIG. 8 shows a linear curve of the correlation observed between the activity level of plasma factor VII (x axis) and the area under the curve measured in the subjects (y axis). The correlation coefficient r2 is excellent: r2=0,883.

The activity level of factor VII was measured by a chronometric method on an automated coagulometer based on the principle of measuring the clotting time (APTT) of a mixture composed of plasma from the patient and plasma deficient in factor VII.

It is well known that the activity level of plasma factor VII is less than 1% in patients with severe hemophilia A, 1 to 5% in those with moderate hemophilia A, and 5 to 40% in those with mild hemophilia A. (White G C II et al., 2001). The values above 40% were determined in samples from non-hemophilic subjects.

As demonstrated above, the value for the area under the curve depends on the severity of the clotting anomaly.

By relating the activity level of factor VIII to the value for area under the curve, it was possible to determine that there is a direct relation between the activity level of clotting factor VIII and the value for area under the curve measured by the method according to the invention.

Example 5. Confirmation of Results in Larger Cohorts

The same experimental protocol as that presented in example 1 was carried out, with the addition of 1 pM of tissue factor to the reaction medium. The tests previously carried out in small numbers of subjects were reproduced in larger cohorts. The threshold value for area under the curve of 4000 AUC was confirmed in these large cohorts.

FIG. 9 shows the relevance of this threshold value of 4000 AUC in samples from 23 healthy subjects and 42 subjects with hemophilia, including all types and severities of the disease: all of the subjects with hemophilia show AUC values below the threshold curve at 4000 AUC.

The mean value for area under the curve in the healthy subjects (controls) is 5930, while the mean value for area under the curve obtained in the samples from the subjects with hemophilia is 1192. Statistical analysis of the difference observed between the values for samples from healthy subjects and those with hemophilia shows a highly significant result (p<0.0001).

Example 6. Diagnosis of Hemophilia a by the Method According to the Invention The experimental protocol of example 1, with a final concentration of 1 pM of tissue factor, was carried out in order to distinguish subjects with hemophilia A, with several severity levels of the disease.

The subjects with hemophilia A are classified as follows:
severe hemophilia A: level of factor VIII activity is less than 1% of normal activity;
moderate hemophilia A: level of factor VIII activity is 1% to 5%;
mild hemophilia A: level of factor VIII activity is 5% to 40%.

The individual results obtained are shown in FIG. 10, and the mean values are shown in Table 3 below:

TABLE 3

|  | Controls | Subjects with severe hemophilia | Subjects with moderate hemophilia | Subjects with mild hemophilia |
|---|---|---|---|---|
| Mean AUC | 5930 | 426 | 840 | 1861 |
| Size of group tested | 23 | 9 | 10 | 8 |

Example 7. Diagnosis of Hemophilia B by the Method According to the Invention The experimental protocol of example 1, with a final concentration of 1 pM of tissue factor, was carried out in order to distinguish the subjects with hemophilia B, with several severity levels of the disease.

The subjects with hemophilia B are classified as follows:
severe hemophilia B: factor IX level is less than 1% of the level of activity normally observed, without any clotting anomaly;
moderate hemophilia B: factor IX level is 1% to 5%;
mild hemophilia B: factor IX level is 5% to 40%.

The individual results obtained are shown in FIG. 11, and the mean values are shown in Table 4 below:

TABLE 4

|  | Controls | Subjects with severe hemophilia | Subjects with moderate hemophilia | Subjects with mild hemophilia |
|---|---|---|---|---|
| Mean AUC | 5930 | 768 | 938 | 2669 |
| Size of group tested | 23 | 3 | 7 | 3 |

Example 8. Direct Correlation Between the Factor IX Level and the Value for Area Under the Curve FIG. 12 shows a linear curve of the correlation observed between the level of plasma factor IX activity (x axis) and the area under the curve measured in the subjects (y axis).

The level of factor IX activity was measured by a chronometric method on an automated coagulometer based on the principle of measuring the clotting time (APTT) of a mixture composed of plasma from the patient and plasma deficient in factor IX.

It is well known that the level of factor IX activity is less than 1% in patients with severe hemophilia, 1 to 5% in those with moderate hemophilia, and 5 to 40% in those with mild hemophilia. (White G C II et al., 2001). Values above 40% were determined in samples from non-hemophilic subjects.

As demonstrated above, the value for the area under the curve depends on the severity of the clotting anomaly.

BIBLIOGRAPHIC REFERENCES

U.S. Pat. No. 8,877,510
EP 2 182 345
Lang T, Bauters A, Braun S L, et al. *Multi-centre investigation on reference ranges for ROTEM thromboelastometry*. Blood Coagul Fibrinolysis 2005; 16: 301-10.
White G C II, Rosendaal F, Aledort L M, Lusher J M, Rothschild C, Ingerslev J. *Definitions in hemophilia. Recommendation of the scientific subcommittee on factor VIII and factor IX of the scientific and standardization committee of the International Society on Thrombosis and Haemostasis*. Thromb Haemost. 2001 March; 85 (3): 560

The invention claimed is:
1. A method for diagnosing anomalies in blood clotting, comprising the following successive steps:
 a) placing a whole blood sample in a receptacle containing two pairs of electrodes connected to a device generating an electric current;
 b) incubating this sample for 60 to 180 seconds in the presence of calcium;

c) adding to this sample tissue factor in a final concentration of 0.5 to 5 pM to initiate blood clotting;

d) measuring the impedance variation between the electrodes as a function of time for a period of 10 to 30 minutes from step (c) and generating a curve of the impedance values as a function of time;

e) comparing the value for the area under the curve generated in step (d) with a value of an area under a reference curve; and f) diagnosing an anomaly in blood clotting with the comparison of the value for the area under the curve generated in step (d) with a value of an area under a reference curve.

2. The method as claimed in claim 1, wherein measurement of the impedance variation is carried out for a period of about 20 minutes.

3. The method as claimed in claim 1, wherein the whole blood sample is citrated.

4. The method as claimed in claim 1, wherein the volume of the whole blood sample is less than 1 ml.

5. The method as claimed in claim 1, wherein in step (b), a saline solution comprising calcium is added to the sample.

6. The method as claimed in claim 1, wherein the reference curve is a mean curve obtained by carrying out steps (a) through (d) on blood samples from subjects without a clotting anomaly.

7. The method as claimed in claim 1, wherein the impedance variation is measured once per minute to generate the curve.

8. The method as claimed in claim 1, wherein the diagnosed clotting anomalies are disorders of secondary hemostasis.

9. A method for determining the efficacy of a coagulant or anticoagulant treatment of a blood clotting anomaly in a subject, comprising the following steps:

i) determining the value for the area under the curve of impedance of a blood sample from said subject before the beginning of said treatment by carrying out the steps of:
  a) placing the blood sample, from said subject before the beginning of said treatment, in a receptacle containing two pairs of electrodes connected to a device generating an electric current;
  b) incubating this sample for 60 to 180 seconds in the presence of calcium;
  c) adding to this sample a tissue factor in a final concentration of 0.5 to 5 pM;
  d) measuring the impedance variation between the electrodes as a function of time for a period of 10 to 30 minutes from step (c) and generating a curve of the impedance values as a function of time, ii) treating the subject with said treatment, and iii) determining the value for the area under the curve of impedance of a blood sample from said subject after the beginning of step ii) by carrying out the steps of:
  a) placing the blood sample, from said subject after the beginning of said treatment, in a receptacle containing two pairs of electrodes connected to a device generating an electric current;
  b) incubating this sample for 60 to 180 seconds in the presence of calcium;
  c) adding to this the sample tissue factor in a final concentration of 0.5 to 5 pM;
  d) measuring the impedance variation between the electrodes as a function of time for a period of 10 to 30 minutes from step (c) and generating a curve of the impedance values as a function of time, with said treatment being considered effective when the value for the area under the curve of impedance determined in step iii) is greater than the value for the area under the curve of impedance determined in step i).

10. The method as claimed in claim 1, wherein the volume of the whole blood sample is less than 500 µl.

11. The method as claimed in claim 1, wherein in step (b), a saline solution comprising calcium is added to the sample by carrying out a vol/vol dilution.

12. The method as claimed in claim 8, wherein the disorders of secondary hemostasis are selected among the congenital coagulopathies and the acquired coagulopathies.

13. The method as claimed in claim 1, wherein, at step d), measurement of the impedance variation is carried out for a period of at least 15 minutes from step (c).

14. The method as claimed in claim 13, wherein the diagnosed clotting anomalies are disorders of secondary hemostasis.

15. The method as claimed in claim 1, wherein the tissue factor is added to the sample in a final concentration of 1 pM to 2 pM.

16. The method as claimed in claim 2, wherein the diagnosed clotting anomalies are disorders of secondary hemostasis.

17. The method as claimed in claim 9, wherein the blood clotting anomaly is a disorder of secondary hemostasis.

18. The method as claimed in claim 1, wherein the sample is incubated for 90 to 180 seconds in the presence of calcium.

19. The method as claimed in claim 1, wherein the sample is incubated for 90 to 150 seconds in the presence of calcium.

20. The method as claimed in claim 1, wherein the tissue factor is added to the sample in a final concentration of 1 pM or 2 pM.

* * * * *